(12) United States Patent
Radhakrishnan et al.

(10) Patent No.: US 12,046,364 B2
(45) Date of Patent: *Jul. 23, 2024

(54) SYSTEM AND METHOD FOR A PATIENT DASHBOARD

(71) Applicant: Board of Regents of the University of Texas System, Austin, TX (US)

(72) Inventors: Hari Radhakrishnan, Houston, TX (US); John B. Holcomb, Bellaire, TX (US); Charles E. Wade, Houston, TX (US); Bryan Cotton, Katy, TX (US); Rondel Albarado, Houston, TX (US); Drew Kraus, Friendswood, TX (US); Joel Watts, Houston, TX (US); Binod Shrestha, Houston, TX (US); Laura J. Moore, Houston, TX (US)

(73) Assignee: BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/681,376

(22) Filed: Feb. 25, 2022

(65) Prior Publication Data
US 2022/0254486 A1  Aug. 11, 2022

Related U.S. Application Data

(63) Continuation of application No. 14/775,467, filed as application No. PCT/US2014/023329 on Mar. 11, 2014, now Pat. No. 11,309,079.
(Continued)

(51) Int. Cl.
*G16H 40/63* (2018.01)
*G16H 10/60* (2018.01)
(Continued)

(52) U.S. Cl.
CPC ............ *G16H 40/63* (2018.01); *G16H 10/60* (2018.01); *G16H 15/00* (2018.01); *G16H 40/67* (2018.01); *G16H 50/20* (2018.01); *G16H 70/20* (2018.01)

(58) Field of Classification Search
CPC ......... G16H 10/60; G16H 40/67; G16H 50/20
(Continued)

(56) References Cited

U.S. PATENT DOCUMENTS

| 2007/0106754 | A1* | 5/2007 | Moore | G16H 40/20 707/E17.116 |
| 2007/0185739 | A1* | 8/2007 | Ober | G16H 50/20 600/301 |
| 2012/0232520 | A1* | 9/2012 | Sloan | G01N 33/48792 604/504 |

FOREIGN PATENT DOCUMENTS

EP   2093684 A2 *  8/2009 ............. G16H 40/63

OTHER PUBLICATIONS

Arinze, Paula; Program Evaluation Dashboard Design and Development for Missouri Telehealth Network Show-Me Echo Program; University of Missouri—Columbia, ProQuest Dissertations Publishing, 2022. 29167923. (Year: 2022).*
(Continued)

*Primary Examiner* — Hiep V Nguyen
(74) *Attorney, Agent, or Firm* — Sprinkle IP Law Group

(57) ABSTRACT

Embodiments disclosed herein provide a system, method, and computer program product for providing a patient dashboard system in a patient care setting. The patient dashboard system collects and stores patient data from a variety of sources. The collected patient data is filtered, analyzed, and displayed. The patient dashboard system displays patient data that is relevant to the treatment of the
(Continued)

patient, including recommended medical actions and pertinent positives and pertinent negatives.

20 Claims, 7 Drawing Sheets

Related U.S. Application Data

(60) Provisional application No. 61/780,174, filed on Mar. 13, 2013.

(51) Int. Cl.
    *G16H 15/00*     (2018.01)
    *G16H 40/67*     (2018.01)
    *G16H 50/20*     (2018.01)
    *G16H 70/20*     (2018.01)

(58) Field of Classification Search
    USPC .......................................................... 705/3
    See application file for complete search history.

(56) References Cited

OTHER PUBLICATIONS

Examination Report issued by the Canadian Intellectual Property Office (CIPO) for Canadian Patent Application No. 2,904669, mailed Oct. 14, 2022, 5 pages.

\* cited by examiner

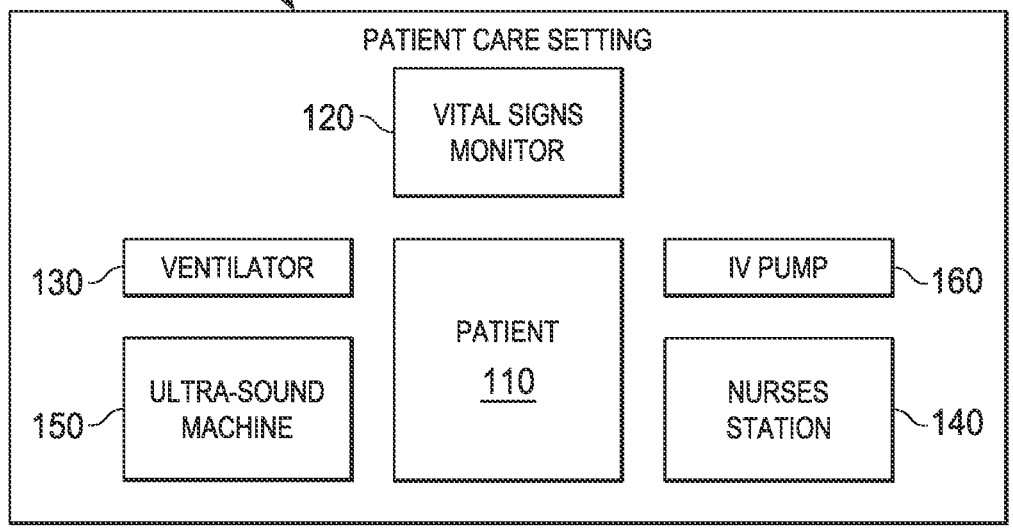
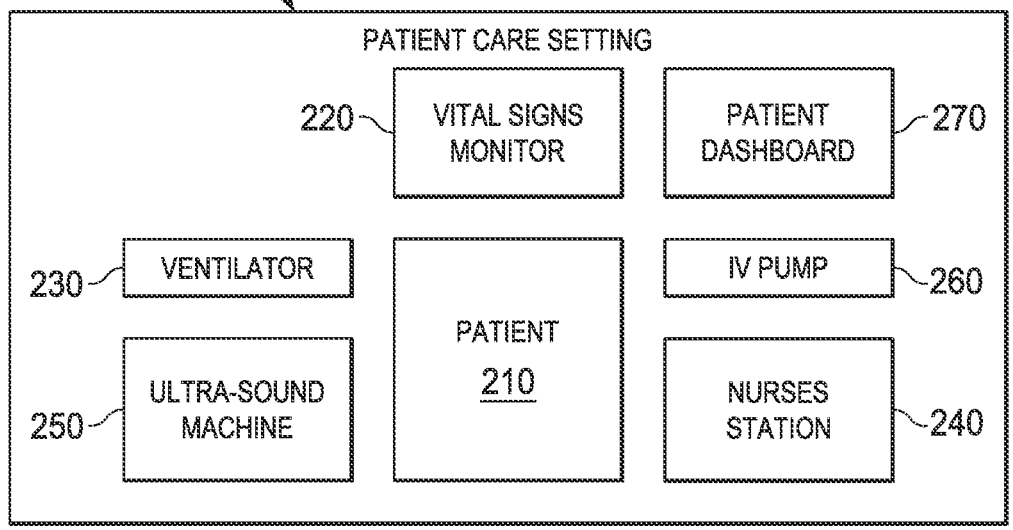

FIG. 7

ED BAY #1 - ONLINE

| 00:01:29 ROCURONIUM |
| 00:01:03 INTUBATION |
| 00:00:01 CHEST TUBE - L |

V2.1.1+35 (4EC8013-DEV)

| RBC | FFP | RBC |
| 3 | 6 | 1 |
| 00:00:12 | 00:00:13 | 00:00:05 |

00:04:23

HR: 123   00:00:28
SBP: 100  00:00:28

GCS: 5   E: 1  V: 2  M: 2
00:00:44

FAST
POSITIVE

ABC+: 2
POSITIVE

CRYSTALLOID: 600CC

--:--:-- CONSULT NEUROSURGERY
--:--:-- CONSIDER ICP
00:01:05 INTUBATE
00:00:54 CALL BLOOD BANK (4-3640)

PATIENT: XRAY0123 - M - 54

NURSE: S., BINOD

FIG. 8

Stress Ulcer Prophylaxis

| # | Task |
|---|---|
| 1 | Patient Medically Ventilated |
| 2 | Platelet Count < 5000 |
| 3 | INR > 1.5 |
| 4 | GCS < 10 |
| 5 | ISS > 16 |
| 6 | Spinal Cord Injury |
| 7 | Stress Ulcer Prophylaxis Medication |

Glucose Control

| # | Task |
|---|---|
| 1 | Recent Fasting Sugar Measurement |
| 2 | Insulin Administered |

Thromboembolic Prophylaxis

| # | Task |
|---|---|
| 1 | Compression Stockings (TED) |
| 2 | Pneumatic Compression Device (SCD) |
| 3 | VTE Prophylaxis |

Head of Bed Elevation

| # | Task |
|---|---|
| 1 | Does Patient Have Spinal Injury? |
| 2 | Is Bed at 30-45 Degree Angle? |

Sepsis Screening

| # | Task |
|---|---|
| 1 | WBC: 14, Bands 10 |
| 2 | Temperature: 102.2 |
| 1 | PaCO2: 30 |
| 2 | Heart Rate: 92 |

Feeding

| # | Task |
|---|---|
| 1 | Feeding access placed |
| 2 | Recent Nutrition Labs |
| 3 | Nutrition Requirements Calculated |
| 4 | Recent Gastric Residuals Measurement |
| 5 | Tube Feeds at Goal |

Analgesia

| # | Task |
|---|---|
| 1 | Recent Assessment of Pain |
| 2 | Pain Medication Administration |

Sedation

| # | Task |
|---|---|
| 1 | RAAS Score |
| 2 | Delirium Measurement |

TRANSFUSIONS

| PATIENT | TYPE | UNITS | LOCATION | TIME |
|---|---|---|---|---|
| XRAY0002 | PLT | 1 | ED BAY #2 | 00:01:23 |
| XRAY0002 | FFP | 1 | ED BAY #2 | 00:01:02 |
| XRAY0002 | RBC | 1 | ED BAY #2 | 00:00:58 |
| NEW PATIENT | FFP | 1 | | PREHOSPITAL |
| NEW PATIENT | RBC | 1 | | PREHOSPITAL |
| XRAY0002 | FFP | 1 | ED BAY #2 | 00:00:51 |
| NEW PATIENT | FFP | 1 | | PREHOSPITAL |
| XRAY0002 | RBC | 1 | ED BAY #2 | 00:00:48 |
| NEW PATIENT | RBC | 1 | | PREHOSPITAL |
| NEW PATIENT | FFP | 1 | | PREHOSPITAL |
| NEW PATIENT | FFP | 1 | | PREHOSPITAL |
| XRAY0002 | FFP | 1 | ED BAY #2 | 00:00:32 |
| NEW PATIENT | RBC | 1 | | PREHOSPITAL |
| XRAY0002 | RBC | 1 | ED BAY #2 | 00:00:28 |
| NEW PATIENT | FFP | 1 | | PREHOSPITAL |
| NEW PATIENT | RBC | 1 | | PREHOSPITAL |
| NEW PATIENT | RBC | 1 | | PREHOSPITAL |
| NEW PATIENT | FFP | 1 | | PREHOSPITAL |
| NEW PATIENT | RBC | 1 | | PREHOSPITAL |
| XRAY0002 | RBC | 1 | ED BAY #2 | PREHOSPITAL |
| XRAY0002 | FFP | 1 | ED BAY #2 | PREHOSPITAL |
| XRAY0002 | RBC | 1 | ED BAY #2 | PREHOSPITAL |
| NEW PATIENT | PLT | 1 | | PREHOSPITAL |
| NEW PATIENT | FFP | 1 | | PREHOSPITAL |

FIG. 9

SYSTEM AND METHOD FOR A PATIENT DASHBOARD

CROSS-REFERENCE TO RELATED APPLICATION(S)

This application is a continuation of, and claims a benefit of priority under 35 U.S.C. 120 of, U.S. patent application Ser. No. 14/775,467 filed Sep. 11, 2015, entitled "SYSTEM AND METHOD FOR A PATIENT DASHBOARD," issued as U.S. Pat. No. 11,309,079, which is a national stage application of International Application No. PCT/US2014/023329, filed Mar. 11, 2014, entitled "SYSTEM AND METHOD FOR A PATIENT DASHBOARD," and claims a benefit of priority from U.S. Provisional Application No. 61/780,174, filed Mar. 13, 2013, entitled "SYSTEM AND METHOD FOR A PATIENT DASHBOARD." This application relates to PCT Patent Application No. PCT/US2014/019878, filed Mar. 3, 2014, entitled "SYSTEM AND METHOD FOR DETERMINING TRIAGE CATEGORIES," which claims a benefit of priority from U.S. Provisional Application No. 61/772,172, filed Mar. 4, 2013, entitled "SYSTEM AND METHOD FOR DETERMINING TRIAGE CATEGORIES." All applications listed in this paragraph are incorporated by reference as if set forth herein in their entireties.

STATEMENT REGARDING FEDERALLY SPONSORED RESEARCH OR DEVELOPMENT

This invention was made with government support under grant number W911QY-10-C-0197 awarded by the U.S. Office of Naval Research. The U.S. government has certain rights in the invention.

TECHNICAL FIELD

This disclosure relates generally to the field of medical informatics. More specifically, the disclosure relates to the computerized determination and display of patient related data in a medical setting. Even more particularly, the disclosure relates to collecting, saving and filtering of patient data, the analysis of such data, the provisioning of decision assist for the medical care of a patient, and the display of information relating to patient data.

BACKGROUND OF THE RELATED ART

Current information technology (IT) support for patient care is lacking in many critical areas. In essence, a large gap exists between the promise of the electronic medical record (EMR) and its execution. At present, medical devices do not integrate together into a cohesive system. Typically, in a patient care setting, multiple disparate sources of data are provided on separate terminals on separate displays or not displayed at all. Physicians or other medical care providers spend a great deal of time moving from system to system and often use paper to aggregate the data required for patient care. This system is inefficient, slow, and often leads to duplication and erroneous data sets. Another complication of this current system occurs with the data not being readily accessible or usable by a machine system to provide clinical decision support. Patients with similar diseases and illnesses may require similar "bundles" of therapy. Human nature makes it difficult for doctors to remember every item in the bundle, let alone complete these bundles in a manner that is consistent with evidence based medical practice.

Moreover, the way data is currently presented, data is available only in an isolated format (e.g., only on the monitor associated with that vital sign) and on a point in time bases. In other words, if a physician is not actively looking at a particular monitor at particular moment in time important data (e.g., a spike in heart rate) may be missed. Part and parcel with this deficiency then, is the problem that because the data is presented in this manner historical data may be unavailable and, because such historical data is unavailable, trend analysis of patient data may be substantially impossible. Additionally, the lack of historical data may impede the ability to evaluate disparate data (e.g., lab values and heart rate) in tandem to assess a patient's condition.

Thus, while a wide variety of detailed data may be available about a particular patient, this data may not be coordinated or presented effectively. Specifically, there may not be any indication of the importance of the data presented or the data presented may not be coordinated with a patient's medical condition. Accordingly, the presented data may not be effective in assisting a physician in assessing a patient's condition or making medical decisions.

In view of challenges in efficiently and effectively using information from a plurality of disparate systems in a patient care setting, there is a need for innovations and improvements.

SUMMARY OF THE DISCLOSURE

Embodiments disclosed herein provide a system and method for collecting, storing, filtering, analyzing, and displaying medical data relating to a patient. In some embodiments, the medical data may be collected from verbal communications and for example, patient hand-offs, physical exams, medical devices, or a combination thereof. Patient hand-off is a term physicians and nurses use when they inform the oncoming physician, who is in the same department and will be assuming care for the patient, what has happened. This occurs usually when one physician is leaving and his/her shift has ended. Some embodiments provide a plurality of guidelines relating to procedures and protocols for treating patients. Based on the medical data collected, a subset of the plurality of guidelines is selected, and medical recommendations are automatically generated by applying the collected medical data to the subset of guidelines.

Embodiments disclosed herein can provide many advantages. For example, by automatically generating the most relevant medical recommendations, compliance to guidelines can be increased. By storing collected medical data, the collected data can be referenced at a future time to help diagnose and treat patients. By providing a display showing various collected medical data, a medical care provider is provided with the best available information at all times, allowing the medical care provider to treat the patient in the best way possible.

BRIEF DESCRIPTION OF THE DRAWINGS

The drawings accompanying and forming part of this specification are included to depict certain aspects of the invention. A clearer impression of the invention, and of the components and operation of systems provided with the invention, will become more readily apparent by referring to the exemplary, and therefore nonlimiting, embodiments illustrated in the drawings, wherein identical reference numerals designate the same components. Note that the features illustrated in the drawings are not necessarily drawn to scale.

FIG. 1 is a block diagram depicting a patient care setting.

FIG. 2 is a block diagram depicting a patient care setting, including a patient dashboard system.

FIG. 7 is a depiction of one embodiment of a patient dashboard.

FIG. 8 is a depiction of one embodiment of a patient dashboard.

FIG. 9 is a depiction of one embodiment of a patient dashboard.

DETAILED DESCRIPTION

Figure 3:
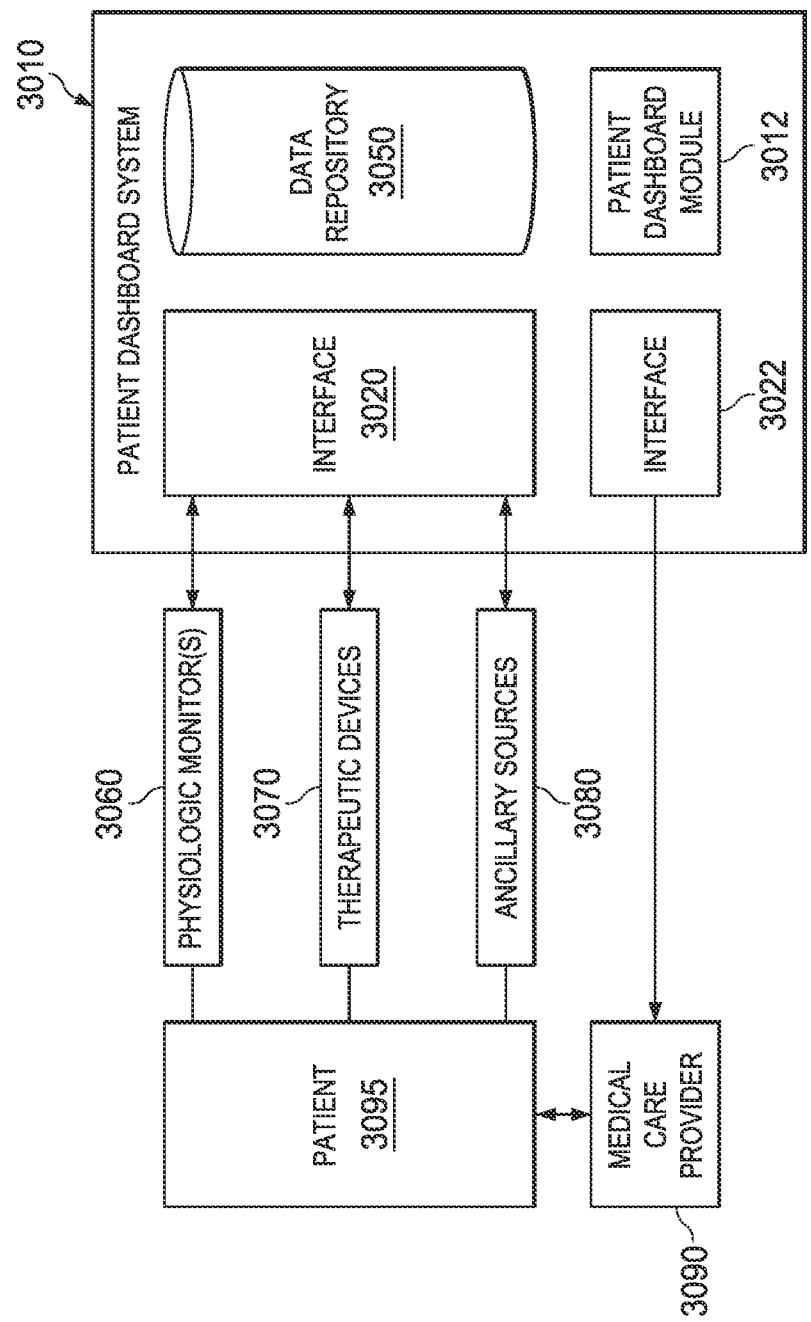
FIG. 3 is a block diagram representing one embodiment of an architecture for implementation of a patient dashboard.

The invention and the various features and advantageous details thereof are explained more fully with reference to the nonlimiting embodiments that are illustrated in the accompanying drawings and detailed in the following description. Descriptions of well known starting materials, processing techniques, components and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure. Embodiments discussed herein can be implemented in suitable computer-executable instructions that may reside on a computer readable medium (e.g., a HD), hardware circuitry or the like, or any combination.

Before discussing specific embodiments, embodiments of a hardware architecture for implementing certain embodiments is generally described herein and will be discussed in more detail later. One embodiment can include one or more computers communicatively coupled to a network. As is known to those skilled in the art, the computer can include a central processing unit ("CPU"), at least one read-only memory ("ROM"), at least one random access memory ("RAM"), at least one hard drive ("HD"), and one or more input/output ("I/O") device(s). The I/O devices can include a keyboard, monitor, printer, electronic pointing device (such as a mouse, trackball, stylus, etc.), or the like. In various embodiments, the computer has access to at least one database over the network.

Each of ROM, RAM, and HD is a tangible computer readable medium for storing computer-executable instructions executable by the CPU. Within this disclosure, the term "computer-readable medium" is not limited to ROM, RAM, and HD and can include any type of data storage medium that can be read by a processor. In some embodiments, a tangible computer-readable medium may refer to a data cartridge, a data backup magnetic tape, a floppy diskette, a flash memory drive, an optical data storage drive, a CD-ROM, ROM, RAM, HD, or the like.

At least portions of the functionalities or processes described herein can be implemented in suitable computer-executable instructions. The computer-executable instructions may be stored as software code components or modules on one or more computer readable media (such as non-volatile memories, volatile memories, DASD arrays, magnetic tapes, floppy diskettes, hard drives, optical storage devices, etc. or any other appropriate computer-readable medium or storage device). In one embodiment, the computer-executable instructions may include lines of complied C++, Java, HTML, or any other programming or scripting code.

Additionally, the functions of the disclosed embodiments may be implemented on one computer or shared/distributed among two or more computers in or across a network. Communications between computers implementing embodiments can be accomplished using any electronic, optical, radio frequency signals, or other suitable methods and tools of communication in compliance with known network protocols.

As used herein, the terms "comprises," "comprising," "includes," "including," "has," "having" or any other variation thereof, are intended to cover a non-exclusive inclusion. For example, a process, process, article, or apparatus that comprises a list of elements is not necessarily limited to only those elements but may include other elements not expressly listed or inherent to such process, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," "in one embodiment."

A brief discussion of context, particularly with respect to treating trauma patients, may be helpful. As mentioned above, current IT support for patient care is lacking in many critical areas. In typical patient care settings, medical devices do not integrate together into a cohesive system. Data sources in a typical patient care setting may include devices that determine vital signs, imaging devices, heart monitors, patient charts, report of labs values, the patient, IV pumps, etc.

FIG. 1 is a block diagram illustrating an exemplary patient care setting 100 (e.g., a trauma center). In FIG. 1, six examples of disparate sources of data are depicted, including a patient 110, a vital signs monitor 120, a ventilator 130, a nurse's station 140 (where a nurse or other medical care professional records patient related information on paper or into a computer), an ultra-sound machine 150, and an IV pump 160. As may be imagined, are wide variety of other data sources may also be a part of the patient care setting that are not depicted in FIG. 1. As can be seen, the patient care setting 100 creates numerous data sources (which may have separate passwords) on separate terminals and on separate displays. As mentioned above, physicians and other medical care providers spend a great deal of time moving from system to system and often use paper to aggregate the data required for patient care.

Also, data from the various data sources is available only in isolated formats and on a point in time basis. For example, typical vital signs monitors, invasive monitoring, ventilators, ultra-sound machines, medical scoring systems, and patient assessments, etc., provide real-time information to a user, but the information is not stored, and if not viewed by a user, the information is lost, unless viewed by a user and manually documented at the nurse's station.

To address the deficiencies described above, among others, attention is now directed to embodiments of systems and methods for a patient dashboard. FIG. 2 is a block diagram illustrating an exemplary patient care setting 200 similar to the patient care setting depicted in FIG. 1, with the addition of a patient dashboard system. In FIG. 2, six examples of disparate sources of data are depicted, including a patient 210, a vital signs monitor 220, a ventilator 230, a nurse's station 240, an ultra-sound machine 250, and an IV pump 260. In addition, a patient dashboard 270 (described in detail below) is provided in the patient care setting 200. The patient dashboard 270 can be mounted on a wall, placed on a surface (counter, table, desktop, etc.), or positioned in any other desired location. In some embodiments, multiple patient dashboards can be used to make the information displayed on the patient dashboards more available to medical care professionals. In other embodiments, one or more patient dashboards can also be provided remotely to allow other medical care professionals to monitor the information displayed.

Generally, a patient dashboard, such as patient dashboard 270 shown in FIG. 2, may be configured to automatically present patient data in a meaningful manner that is effective in improving patient outcomes. More particularly, embodiments as described herein may serve to collect data from a variety of sources and collate such data. The collected data can be saved in a repository. The collected data can also be filtered, enabling only the most pertinent data to be used by the system (described in detail below). The collected data can be analyzed using any number of algorithms or interpreted in a particular manner to determine if any medical actions should be recommended and/or to determine pertinent positives or negatives relating to the patient's medical condition. The pertinent positives or pertinent negatives, along with any recommended medical actions to assist in decision making, may be presented to users through an interface, such as a display. The process of collecting data, filtering data, analyzing data, and displaying information can be performed automatically without user intervention. In some examples, a user may configure or customize the collecting, filtering, analyzing, reference ranges/values, and/or displaying steps.

The presentation of information may include displaying desired medical data or displaying recommendations with visual (or auditory, etc.) indicators of the importance of the data or the severity of a patient's condition. Accordingly, using embodiments as described herein, pertinent patient data and decision recommendations may be determined and presented substantially in real-time. Real-time and effective presentation of such information is not possible in conventional systems, as the volume of data and complexity of analysis and decision recommendation is prohibitively complex without using the techniques described herein.

The embodiments described below provide relevant, context sensitive information that may provide decision assist by providing medical recommendations to a medical care provider. These exemplary embodiments may be implemented in, or tailored to, a wide variety of settings such as a trauma center, an ICU, a cardiac wing or floor, a pre-hospital setting or any other desired setting. In some examples, the patient dashboard interface may be customizable by a medical care provider such that the data displayed or the method of display is configured to a users desires, local practice patterns, local institutions, or for any other reasons. Furthermore, the patient dashboard interface may be provided to any desired device, such as a bedside display (e.g., a television, a computer monitor, a projected image, other desired display devices, etc.), a device of the medical care provider (e.g., a smartphone, a tablet, a wearable computer with an optical head-mounted display, etc.), a display in a monitoring station in another location (e.g., a monitoring room in a hospital, etc.), etc. In this way, medical recommendations can be actively transmitted to targeted medical care providers as appropriate, causing their devices to display the medical recommendations determined by embodiments disclosed herein (e.g., directed page, text message, phone call to an attending physician if a critical recommendation, to a resident physician for a routine non-critical recommendation, etc.). Example embodiments for determining medical recommendations are described below with reference to FIG. 5. Thus, those skilled in the art will appreciate that embodiments of a patient dashboard disclosed herein may be customizable for local institutions and local practice patterns. Moreover, a patient dashboard can be implemented in a wide variety of settings and effectively utilized no matter what data is available.

A patient dashboard described above can be implemented using any desired architecture. FIG. 3, a high-level block diagram illustrating one example of an architecture used in the implementation of one embodiment of a patient dashboard. In the example shown in FIG. 3, a patient dashboard system 3010 is shown. The patient dashboard 3010 may comprise one or more computing devices operable to execute a patient dashboard module 3012 configured to implement a patient dashboard for an aspect of care (e.g., trauma, ICU, stroke, cardiac, etc.). The patient dashboard system 3010 includes interfaces 3020 and 3022 for interfacing with various desired devices and systems. In the example shown, interface 3020 is shown linked to one or more medical devices such as physiological monitor(s) 3060. Examples of physiological monitor(s) 3060 include, but are not limited to, vital sign monitors, imaging machines, etc. Interface 3020 is also shown linked to one or more therapeutic devices 3070, such as those that administer medications. Interface 3020 is also shown linked to one or more ancillary sources 3080, such as lab results, etc.

The devices linked to interface 3020 of the patient dashboard system 3010 collect data related to a patient 3095, and provide the collected data to the patient dashboard system 3010. The information received by the patient dashboard system 3010 on the patient 3095 is stored in data repository 3050. In one example, the received data is stored in the repository 3050 substantially without the involvement of a medical care provider. The repository 3050 may be comprised of one or more databases located on the computing device of the patient dashboard system 3010 and/or on a remote system or server. The devices that are linked to the interface 3020 may communicate with the patient dashboard system 3010 in any desire manner. For example, one or more medical devices may be able to accept instructions, or communicate, in the Health Level 7 (HL7) Version 3 Messaging Standard and perform one or more actions based on the instructions or return data to the data repository 3050.

Thus, patient data may be received at interface 3020 using HL7 messages. Data may also be provided manually through interface 3020, for example from lab technicians, nurses, etc. In some examples, the data repository 3050 received raw data from the monitors 3060, devices 3070, and sources 3080.

The patient dashboard module 3012 may filter and analyze the data relating to the patient 3095 that is collected in the data repository 3050 and then present data through interface 3022 to a medical care provider 3090 (described in detail below) via a visual display. The data presented to the medical care provider 3090 is based on the data relating to the patient stored in the data repository 3050. In some examples, the patient dashboard module 3012 analyzes the patient data in the data repository 3050 using any number of algorithms to determine if any medical actions should be recommended or if data should be interpreted in a particular manner. The data may also be filtered and interpreted to determine pertinent positives or pertinent negatives for the patient's current medical condition. The pertinent positives or pertinent negatives, along with any recommended medical actions may be presented through interface 3022 to the medical care provider(s) 3090 via a display or other device. The presentation of this information may entail the presentation of certain display prompts, or indicators (e.g., color coding, blinking, etc.) on a visual, verbal or auditory interface device, etc. Based on data or recommendations presented, actions may then be carried out by the medical care provider 3090 such that therapeutic intervention or other action may be performed on the patient 3095, as desired.

Figure 4:
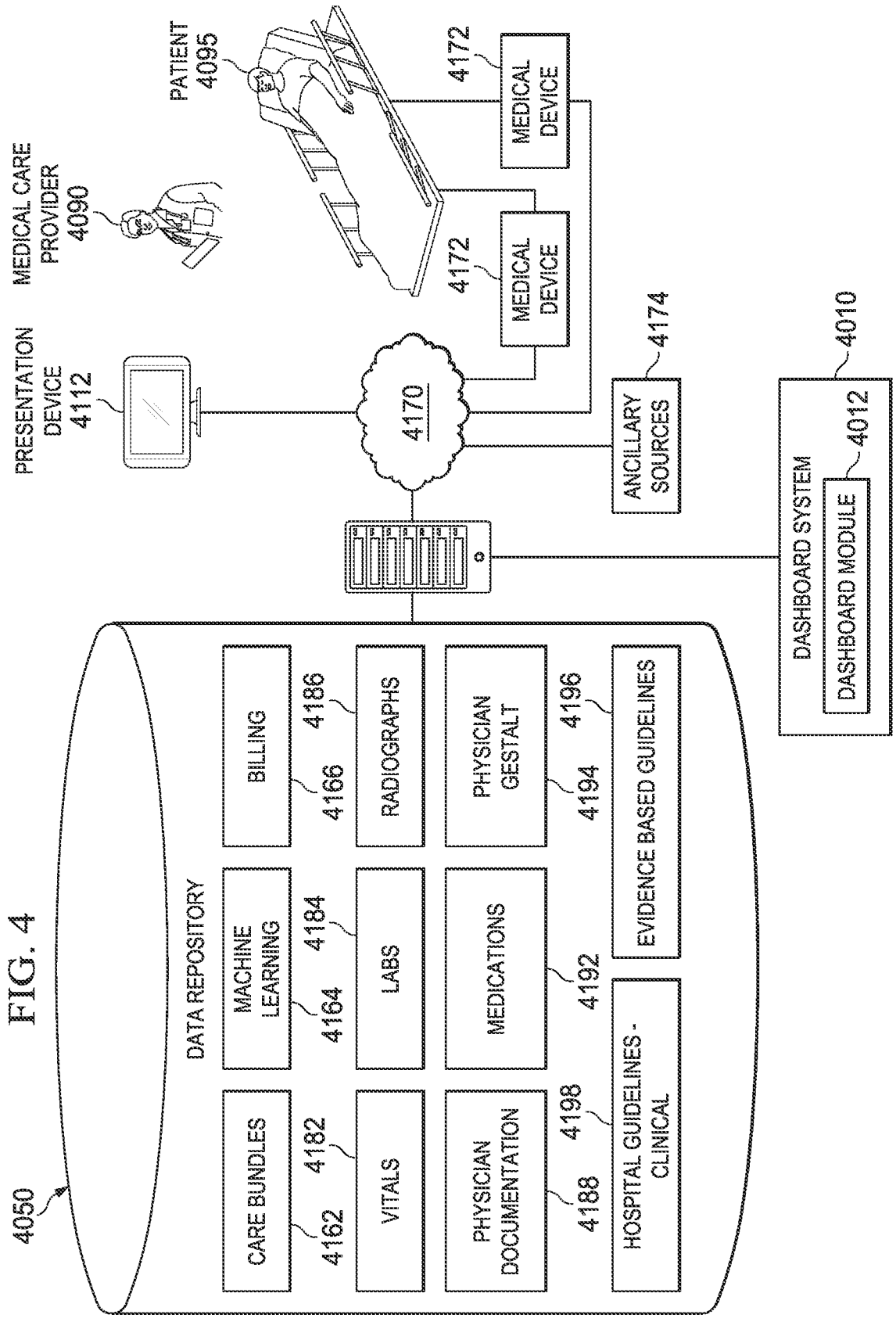
FIG. 4 is a block diagram representing one embodiment of an architecture for implementation of a patient dashboard.

FIG. 4 is a more detailed depiction of an implementation of one embodiment of a patient dashboard. In the example shown in FIG. 4, a patient dashboard system 4010 is shown. In a medical care environment such as a clinical setting, hospital, pre-hospital care, trauma center, ICU, cardiac floor, etc. in which patient care is implemented, it may be desired to implement a patient dashboard to provide pertinent patient data and associated recommendations. To that end, the dashboard system 4010 may be employed in such a clinical setting to aid in the computerized implementation of such a dashboard.

In one embodiment, the dashboard system 4010 is coupled through a wired or wireless communication network 4170, such as a LAN, WAN, Intranet, the Internet, etc. to one or more medical devices 4172, ancillary data sources 4174 or presentation devices 4112. Dashboard system 4 10 may include a patient dashboard module 4012 configured to implement a patient dashboard for an aspect of care (e.g., trauma, ICU, stroke, cardiac, etc.).

Patient dashboard module 4012 may communicate with one or more medical devices 4172 or ancillary data sources 4174 to obtain data associated with patient 4095 and store such data in data repository 4050. Medical devices 4172 and ancillary data sources 4174 may include, for example, physiological monitors such as vital sign monitors, imaging machines, therapeutic devices such as those that administer medications, labs, etc. In one embodiment, these communications may occur using HL7 messaging or obtained directly from a feed from the respective device 4172. The dashboard module 4012 may present one or more interfaces (e.g., through a computing device coupled to the dashboard system 4010 through network 4170) through which a medical care provider 4090 or other person may enter data associated with the patient.

In some embodiments, the patient data stored in data repository 4050 may include information relating to vitals 4182, labs 4184, radiographs 4186, physician documentation 4188 and medications 4192. Vitals 4182 may include data relating to vital signs obtained from, for example, pre-hospital monitoring, cardiac monitors, non-invasive hemoglobin devices, standard vital sign devices, etc. Physician documentation 4188 may include data obtained from a medical care provider, such as medical care provider 4090 shown in FIG. 4. To obtain such data, medical care provider 4090 may be presented with an interface which is tailored to the patient's medical condition (e.g., trauma, cardiac, ICU, etc.). The medical care provider 4090 can enter data such that the dashboard module 4012 receives such data. This data may then be tagged with semantic tags indicating its meaning to place the data in a machine interpretable format and stored in data repository 4050. Labs 4184 may be data (e.g., values) associated with any tests (e.g., blood draws) performed on the patient 4095. This data may be input using an interface, obtained using messaging, etc. Radiographs 4186 may be any type of imaging (e.g., processed by a radiologist or interpreted by medical care provider, etc.) or interpretation of such imaging. The radiograph data 4186 may include, for example, X-rays, CT-scan, ultrasound (intravascular, FAST), MRI or any other imaging. Medications 4192 may be any medications administered to the patient 4095 or medications the patient 4095 was taking prior to the patient's entry into the clinical setting.

As described above, using patient data collected from medical devices 4172, ancillary sources 4174, and medical care provider 4090, current data about patient 4095 may be collected and stored in data repository 4050. Accordingly, as this data is stored and updated, a historical record of the collected patient data may be accumulated in data repository 4050.

Once the collected patient data is accumulated in the data repository 4050, the dashboard module 4012 may then analyze the data stored in data repository 4050. This analysis may include determining trends on the patient data stored in data repository 4050, for example, based on the historical data associated with the patient 4095. These trends may not just encompass data from a single data source determined over a period of time, but additionally may be analyzed using other historical values for other patient data obtained over time, such that trends may include correlated historical data.

Furthermore, this analysis may include the determination of one or more decision recommendations. This analysis may use physician gestalt 4194, evidence based guidelines 4196, hospital guidelines 4198, and clinical care bundles 4162. Physician gestalt 4194 may be data representing the thought processes of medical care providers and may include actions taken, or recommendations made, by physicians or medical care providers associated with a set of circumstances or patient data. Evidence based guidelines 4196 may be one or more protocols or guidelines which may be used to analyze patient data to determine a recommendation. Such evidence guidelines may be based on the available medical literature and are usually driven by test results or lab values and may include scoring criteria and recommendations based on such scores.

Examples of evidence based guidelines 4196 mentioned above include, for example, those promulgated by in conjunction with Advanced Trauma Life Support (ATLS). Other examples may include: if the GCS (Glasgow Coma Scale) score is less than 8, consider neurosurgery consultation and consider ICP monitor placement; if an abdominal Focused Assessment of Sonography for Trauma (FAST) is positive consider laparotomy; if a cardiac FAST is positive, consider sternotomy; if a thoracic FAST is positive consider chest tube placement; if there is a pelvic fracture and the blood pressure is less than 100 mmHg, consider a pelvic binder. Other examples of evidence based guidelines are also possible, as those of ordinary skill in the art would understand.

Hospital guidelines 4198 may be specific guidelines associated with a hospital or other setting which may have specific guidelines for taking care of patient based on, for example, hospital capabilities or policies. Clinical care bundles 4162 may be similar to evidence based guidelines that are associated with certain categories of treatment (e.g., sepsis, trauma, etc.). Other guidelines and rules-based procedures may also be used with the patient dashboard system.

Accordingly, dashboard module 4012 may be configured to use machine learning algorithms 4164, physician gestalt 4194, hospital guidelines 4198, and clinical care bundles 4162 to determine one or more recommendations. Dashboard module 4012 may also apply evidence based guidelines 4196 to patient data to determine one or more recommendations. Machine learning algorithms 4164 may include such algorithms as Random Forest, Rotation Forest, LogitBoost, Decision Tree, Logistic Regression, Naïve Bayes, Multilayer Perception, etc. Computationally intensive determinations for recommendations may be made using a large number of inputs by using machine learning algorithms such as those listed above. In fact, such determinations may be made without a medical care provider 4090 even being aware of the number of or complexity of factors being used to make such recommendation. By using such algorithms then, recommendations may be consistently improved (e.g., outcomes may get better) as more and more data is stored in data repository 4050 and used to update or adjust the algorithms. Such improvements may result in a measurable improvement in patient outcomes (e.g., reductions in mortality rates).

Examples of the machine learning algorithms listed above are those that may be used for admission to different levels of care in the hospital (e.g., based on a random forest algorithm) using data collected in pre-hospital or hospital settings. Other examples may include algorithms that use thromboelastogram cutpoints to determine endpoints for care (e.g., transfusion of blood, administration of procoagulants, etc.). Another example of such an algorithm may be to use an ABC Score for identification of patients who will need a massive transfusion (>10 units) of red blood cells based on admission heart rate, blood pressure, FAST exam results, and mechanism (blunt vs. penetrating) of injury.

Dashboard module 4012 may also be configured to determine what data to present through an interface, such as presentation device 4112. The determination of such data may include the filtering of data associated with the patient 4095 stored in data repository 4050 to determine the pertinent positives and the pertinent negatives. These pertinent positives and pertinent negatives may include one or more recommendations for care of the patient (e.g., one or more recommendations determined through machine learning algorithms that were above a certain threshold associated with those algorithms). Exemplary screen shots of a presentation device described below provide examples of pertinent positives/negatives.

In some embodiments, dashboard module 4012 is configured to present the pertinent positives and the pertinent negatives through presentation device 4112. The presentation device 4112 may be comprised of an auto-updating display that substantially continuously updates the pertinent positives and pertinent negatives as they are updated or determined (e.g., as new patient data is collected, new recommendations are determined, etc.). Pertinent positives or pertinent negatives can include, for example, current patient data, trends in patient data, interventions that have not taken place, the patient's nurse, patient's elapsed time in the clinical setting, recommended actions, etc. Accordingly, using the dashboard system 4010, a medical care provider 4090 can easily ascertain at any moment in time what has occurred, pertinent current states, what has not occurred with respect to the patient 4095, and any current recommendations with respect to a given patient. Moreover, the pertinent positives or pertinent negatives may be presented with indicators of data that is relatively more important or critical. For example, certain critical data may be colored red, be blinking, alarms may be sounded, etc.

The dashboard module 4012 may also be configured to make other determinations based on patient data. For example, the dashboard module 4010 may be configured to determine billing information 4166 for medical care providers so care is adequately and properly billed.

Figure 5:
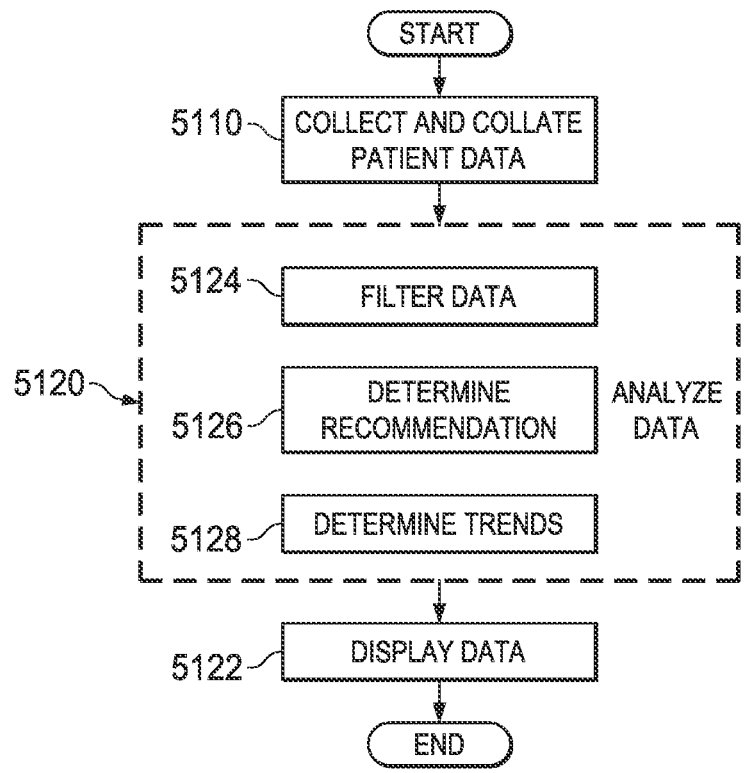
FIG. 5 is a flow diagram representing one embodiment of a method for implementing a patient dashboard.

Referring now to FIG. 5, one embodiment for a method for implementing a patient dashboard is depicted. FIG. 5 is a flowchart illustrating an example of the operation of one example of a patient dashboard. Other examples are also possible. At step S110 data is collected and collated. Data associated with a patient may be received from patient history, physical exams, medical devices, ancillary data sources, or other sources, and stored in a data repository. Medical devices and ancillary data sources may include for example, physiological monitors such as vital sign monitors, imaging machines, therapeutic devices such as those that administer medications, labs, etc. In one embodiment, communications may occur using HL7 messaging, obtained directly from a feed from a device or using interfaces through which data associated with the patient may be entered. Specifically, in one embodiment, the collected patient data may include vitals, labs, radiographs, physician documentation or medications.

As data is collected, it is analyzed (block 5120). In the example shown, the analyze data block is broken into three sub-blocks, including filtering data (step S124), determining recommendations (step S126), and determining trends (step S128). After the data is analyzed (or while the data continuing to be analyzed), the system displays the data (step S122).

As mentioned above, as data is collected, it is filtered (step S120) by the dashboard system. The data may be filtered in any desired manner. The system filters data to determine which data (or what information derived from the data) to present through the interface. The determination of such data may include the filtering of the stored patient data to determine the pertinent positives and the pertinent negatives. These pertinent positives and pertinent negatives may include one or more recommendations for care of the patient (e.g., one or more recommendations determined through machine learning algorithms that were above a certain threshold associated with those algorithms).

In one example, patient data is filtered based on the type of patient. The type of patient can be determined from one or a combination of several sources. For example, information from a patient history (e.g., asking the patient questions) and/or a patient physical exam can be used to determine a patient type or patient category. Patient types can be based on the type of injury or illness. For example, based on the patient history and/or physical exam, if the system determines that the patient is a trauma victim. In addition, in this example, the collected data may further narrow the patient type, for example, trauma with abdominal injuries.

Based on the determination of patient type (described above), the collected data can be further filtered. For example, in the example given (a patient suffering from trauma), the system can filter the collected data and use only the data that is relevant to trauma victims. Also, a typical patient care setting will have sets of guidelines (e.g., evidence based guidelines, hospital guidelines, etc.) that medical care providers are encouraged to follow when treating a patient. A facility, such as a hospital, may typically have hundreds or thousands of guidelines that medical care providers are supposed to follow. The patient dashboard system uses the collected data to filter the guidelines, so that only the relevant guidelines are analyzed. In the example above (where the patient was determined to be a trauma victim), the patient dashboard system can filter through the thousands of guidelines, and only use the guidelines relevant to trauma victims. Within patient type, location-specific (emergency department, ICU, etc.) guidelines may be generated and then discontinued based on the patient's changing location within a hospital or medical center. Patient priorities and delivery of care is a dynamic process and the guidelines for these different areas within a single patient's care can differ quite significantly (e.g., large volume, liberal transfusion policy in the emergency department and operating room, then restrictive policy once hemodynamically stable and in the ICU). This will result in more relevant information provided to the heath care provider, and increase the likelihood of health care providers following the recommended guidelines.

Figure 6:
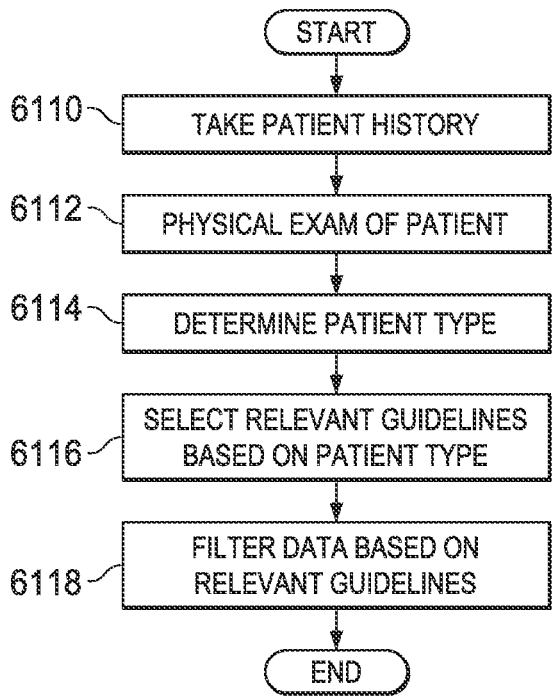
FIG. 6 is a flow diagram representing one embodiment of a method for filtering patient data.

FIG. 6 is a flowchart illustrating one example of the filtering step shown in FIG. 5. Note that numerous other filtering steps may be taken in addition to those shown in FIG. 6, as one skilled in the art would understand. At step 6110, the patient history is taken. The patient history is typically taken early in a patient's stay in a health care facility (and some obtained in the prehospital setting prior to clinical deterioration), and may involve asking the patient questions about symptoms, the circumstances surrounding the source of the trauma or illness, etc. At step 6112, a physical exam of the patient is taken. The physical exam can entail numerous items, such as examining injured areas, noting physical characteristics, taking vital signs, etc. Based on the patient history, physical exam, and any other available information, the patient type is determined (step 6114). For example, it may be determined that the patient suffered trauma, disease, a heart attack, a stroke, etc. In settings where medical care providers have guidelines to guide them in the treatment of a patient, the system can select a subset of the guidelines (i.e., the most relevant guidelines), based on the patient type (step 6116). For example, it if was determined that the patient suffered trauma, a subset of the guidelines most relevant to trauma victims are selected. In addition, based on the patient history or physical exam, certain guidelines may also be selected. For example, if a medical parameter was measured to be out of a predetermined range, one or more guidelines relating to that finding can also be selected. At step 6118, the collected data is filtered based on the selected relevant guidelines. In some examples, thousands of data values may be collected from a patient. However, based on the selected guidelines, only a subset of the collected data may be relevant. At step 6118 the relevant subset of collected data is filtered.

The filtering process may also include various other types of filtering. For example, certain types of information may be provided by multiple devices. The system can handle this type of information in any way desired, including for example, choosing the most reliable data source, averaging values, etc. For example, a patient's respiratory rate may come from multiple sources such as a finger probe, a ventilator, etc. The dashboard system can filter the data such that the value from the most reliable source is used. The filtering process can also be used to recommend certain medical tests. For example, in a given medical facility, it may be possible to provide dozens of radiology tests, thousands of lab tests, measurement of numerous vital signs, limitless physical exams, etc. Based on patient type (e.g., trauma, cardiovascular, stroke, etc.), collected patient data, hospital guidelines, etc., the patient dash board can filter through the thousands of possible tests and provide recommendations that are the most relevant and useful for treating the particular patient.

Referring again to FIG. 5, analysis of the collected data may include determining one or more decision recommendations (step S126) and determining one or more trends in the data (step S128). Determining a decision recommendation at step S026 may, in one embodiment, use physician gestalt, evidence based guidelines, hospital guidelines and/or clinical care bundles. The determinations can also use any other information or guidelines, as desired. Note that the process of filtering and analyzing can be a continuous process. In other words, whether or not data continues to be collected from a patient, the filtering and analysis of data continues and the information displayed on the dashboard is updated in near real-time.

In some embodiments, machine learning algorithms may be applied to determine a recommendation in conjunction with physician gestalt, hospital guidelines or clinical care bundles based on the patient data stored in the data repository. Decision recommendation may also be determined by applying evidence based guidelines to patient data. Computationally intensive determinations for recommendations may be made using a large number of inputs by using machine learning algorithms. In fact, such determinations may be made without a medical care provider even being aware of the number of or complexity of factors being used to make such recommendations. These machine learning algorithms may improve the recommendations provided as more and more data is stored in data repository and used to update or adjust these algorithms. Such improvements may result in a measurable improvement in patient outcomes (e.g., reductions in mortality rates).

The analysis of patient data may also include determining trends on the stored patient data at step S128. These trends may not just encompass data from a single data source determined over a period of time, but additionally may be analyzed using other historical values for other patient data obtained over time, such that trends may include correlated historical data.

The filtered data may then be displayed at step S122. For example, in one embodiment, the pertinent positives and the pertinent negatives may be presented through a presentation device. This presentation device may be, for example, a monitor in a patient care setting (e.g., patient's room, ICU, emergency room, monitoring room or center in a hospital, etc.). Such a display may be substantially continuously updated with the current pertinent positives and pertinent negatives as they are updated or determined (e.g., as new patient data is collected, new recommendations may be determined, etc.). Pertinent positives or pertinent negatives can include, for example, current patient data, trends in patient data, interventions that have not taken place, the patient's nurse, patient's elapsed time in the clinical setting, recommended actions, etc. Accordingly, using such a display, it can be easily ascertained at any moment in time what has occurred (e.g., previous interventions, etc.), pertinent current states, what has not occurred, and any current recommendations with respect to a given patient. Moreover, the pertinent positives or pertinent negatives may be presented with indicators of data that is relatively more important or critical. For example, certain critical data may be colored red, be blinking, alarms may be sounded, etc.

It may now be helpful to an understanding of embodiments described above to look at certain examples of an interface that may be presented as a patient dashboard. Looking first at the example of FIG. 7, one embodiment of a patient dashboard interface that may be presented in a trauma setting, or emergency room, is shown. In other settings, the dashboard will operate in a similar manner, but will display information most relevant to the respective setting. For example, in an ICU setting, the patient dashboard will look similar and operate in the same manner, but will display different information.

In the example of FIG. 7, various patient data is displayed. For example, the patient's current heart rate is displayed. Included are transfusions which the patient have received, displayed in units, including RBC (red blood cell), FFP (fresh frozen plasma) and PLT (platelets) are shown. Such a display can also provide values for the patient's red blood cell (RBC) and blood platelet (PLT) levels. The dashboard can also display the quantity of drugs that the patient has received. In addition, in this example, the values displayed can be color coded based on the values being within a predetermined range. For example, if a given displayed value is out of range, it can be displayed in red to alert the medical care provider to note the value. In the example shown, the patient's ABC (assessment of blood consumption) and focused assessment sonography for trauma (FAST) scores are shown. The exemplary patient dashboard shown in FIG. 7 also shows recommendations automatically generated based on collected and filtered data. In the example shown (in the right-hand column) the dashboard recommends the user to "consult neurosurgery" and "consider ICP." The patient dashboard may be configured to provide any desired recommendation, as one skilled in the art would understand. For example, recommendations can be generated relating to recommended medical procedures, recommended drugs, recommended tests, recommended triage, etc. Recommendations can take the form of text, numerical scores, etc.

As described above, the recommendations provided by the patient dashboard are generated automatically based on collected data and medical guidelines. For a given set of guidelines and algorithms, the same inputs will result in a display of the same outputs and recommendations each time. This enables medical care providers to more accurately follow hospital guidelines. The patient dashboard may also show tasks that have been marked done. In the example shown, the dashboard shows "intubate" and "call blood bank" as done by showing the recommendations with a strikethrough font. The dashboard also shows a patient identifier (lower left corner) and identifies one or more medical care providers (lower right corner). As mentioned above, the information displayed (and not displayed) on the patient dashboard is stored and can be accessed later, if needed. In typical systems, information provided by most medical devices is displayed in real-time and lost, unless manually recorded by a user.

FIG. 8 depicts an embodiment of a patient dashboard that may be utilized in an ICU setting. In this example, the dashboard displays various pieces of information important in treating a patient in an ICU environment. FIG. 9 depicts an embodiment of a patient dashboard that may be utilized to coordinate care with a blood bank setting. In this example, the dashboard displays various pieces of information important in treating a patient with resources obtained from a blood bank environment. For example, a remote display that could be used by blood bank personnel to proactively send blood to the correct location in response to changes in a patient's condition. Patients A blood bank collects blood, isolates and tests blood products, stores them, and meters this precious resource. Blood banks are responsible for the availability and quality of blood products.

In the foregoing specification, the invention has been described with reference to specific embodiments. However, one of ordinary skill in the art appreciates that various modifications and changes can be made without departing from the scope of the invention. Accordingly, the specification and figures are to be regarded in an illustrative rather than a restrictive sense, and all such modifications are intended to be included within the scope of invention.

Although the invention has been described with respect to specific embodiments thereof, these embodiments are merely illustrative, and not restrictive of the invention. The description herein of illustrated embodiments of the invention is not intended to be exhaustive or to limit the invention to the precise forms disclosed herein (and in particular, the inclusion of any particular embodiment, feature or function is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment," "an embodiment," or "a specific embodiment" or similar terminology means that a particular feature, structure, or characteristic described in connection with the embodiment is included in at least one embodiment and may not necessarily be present in all embodiments. Thus, respective appearances of the phrases "in one embodiment," "in an embodiment," or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

Any suitable programming language can be used to implement the routines, methods or programs of embodiments of the invention described herein, including C, C++, Java, assembly language, etc. Different programming techniques can be employed such as procedural or object oriented. Any particular routine can execute on a single computer processing device or multiple computer processing devices, a single computer processor or multiple computer processors. Data may be stored in a single storage medium or distributed through multiple storage mediums, and may reside in a single database or multiple databases (or other data storage techniques). Although the steps, operations, or computations may be presented in a specific order, this order may be changed in different embodiments. In some embodiments, to the extent multiple steps are shown as sequential in this specification, some combination of such steps in alternative embodiments may be performed at the same time. The sequence of operations described herein can be interrupted, suspended, or otherwise controlled by another process, such as an operating system, kernel, etc. The routines can operate in an operating system environment or as stand-alone routines. Functions, routines, methods, steps and operations described herein can be performed in hardware, software, firmware or any combination thereof.

Embodiments described herein can be implemented in the form of control logic in software or hardware or a combination of both. The control logic may be stored in an information storage medium, such as a computer-readable medium, as a plurality of instructions adapted to direct an information processing device to perform a set of steps disclosed in the various embodiments. Based on the disclosure and teachings provided herein, a person of ordinary skill in the art will appreciate other ways and/or methods to implement the invention.

It is also within the spirit and scope of the invention to implement in software programming or of the steps, operations, methods, routines or portions thereof described herein, where such software programming or code can be stored in a computer-readable medium and can be operated on by a processor to permit a computer to perform any of the steps, operations, methods, routines or portions thereof described herein. The invention may be implemented by using software programming or code in one or more general purpose digital computers, by using application specific integrated circuits, programmable logic devices, field programmable gate arrays, optical, chemical, biological, quantum or nano-engineered systems, components and mechanisms may be used. In general, the functions of the invention can be achieved by any means as is known in the art. For example, distributed or networked systems, components and circuits can be used. In another example, communication or transfer (or otherwise moving from one place to another) of data may be wired, wireless, or by any other means.

A "computer-readable medium" may be any medium that can contain, store, communicate, propagate, or transport the program for use by or in connection with the instruction execution system, apparatus, system or device. The computer readable medium can be, by way of example, only but not by limitation, an electronic, magnetic, optical, electromagnetic, infrared, or semiconductor system, apparatus, system, device, propagation medium, or computer memory. Such computer-readable medium shall generally be machine readable and include software programming or code that can be human readable (e.g., source code) or machine readable (e.g., object code).

A "processor" includes any, hardware system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real-time," "offline," in a "batch mode," etc. Portions of processing can be performed at different times and at different locations, by different (or the same) processing systems.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/figures should be considered only as exemplary, and not limiting, unless otherwise specifically noted.

Furthermore, the term "or" as used herein is generally intended to mean "and/or" unless otherwise indicated. As used herein, a term preceded by "a" or "an" (and "the" when antecedent basis is "a" or "an") includes both singular and plural of such term (i.e., that the reference "a" or "an" clearly indicates only the singular or only the plural). Also, as used in the description herein, the meaning of "in" includes "in" and "on" unless the context clearly dictates otherwise.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component.

What is claimed is:

1. A method of analyzing information from disparate sources in a patient care setting and recommending a medical action through a patient dashboard system, the method comprising:
   collecting, by the patient dashboard system from a plurality of sources in a location within the patient care setting, electronic medical data of a patient in the location within the patient care setting, the patient dashboard system having a storage device, a computing device, and a display, the plurality of sources including a physical exam of the patient and medical devices communicatively connected to the patient dashboard system, the electronic medical data comprising a patient type determined based on an injury or illness of the patient;
   storing, by the patient dashboard system, the electronic medical data of the patient in a data repository;

selecting, by the patient dashboard system, based on the patient type and from a plurality of guidelines for treatment of patients, a subset of the plurality of guidelines pertinent to the injury or illness of the patient;

filtering, by the patient dashboard system, the stored electronic medical data of the patient according to the patient type, wherein the filtering produces filtered medical data of the patient, wherein the filtered medical data is associated with the injury or illness of the patient;

determining, by the patient dashboard system from the subset of the plurality of guidelines, a first set of location-specific guidelines based on the location of the patient;

analyzing, by the patient dashboard system, the filtered medical data of the patient associated with the injury or illness of the patient according to the first set of location-specific guidelines pertinent to the injury or illness of the patient;

generating, by the computer patient dashboard system based on the analyzing, one or more recommendations for a medical treatment of the injury or illness of the patient;

determining, by the patient dashboard system based on the patient's changing from the location to a different area, a second set of location-specific guidelines;

applying, by the patient dashboard system, the second set of location-specific guidelines to the filtered medical data of the patient, wherein the applying produces an updated recommendation; and automatically updating, by the patient dashboard system in near real-time, the display with the updated recommendation.

2. The method of claim 1, wherein the interface display of the electronic patient dashboard system comprises a video display device, a monitor, an auto-updated device, or a presentation device.

3. The method of claim 1, wherein the patient care setting comprises a hospital, a trauma center, an emergency room, a floor, an intensive care unit, or a pre-hospital setting.

4. The method of claim 1, wherein the medical devices comprise at least one of an imaging device, labs, medications, a heart monitor, a patient chart, a vital sign monitor, or an intravenous (IV) pump.

5. The method of claim 1, wherein analyzing the filtered medical data of the patient further comprises categorizing the patient.

6. The method of claim 1, further comprising:
prior to applying the second set of location-specific guidelines to the filtered medical data of the patient, discontinuing the first set of location-specific guidelines.

7. The method of claim 1, wherein the location comprises an intensive care unit, an emergency room, an operating room, a patient room, or a monitoring room and wherein the area comprises an intermediate care program (ICP) or a neurosurgery unit.

8. A patient dashboard system for analyzing information from disparate sources in a medical care setting and recommending a medical action, the system comprising:
a storage device;
a display device;
a computing device operatively coupled to one or more sources of electronic medical data; and
a dashboard module installed on the computing device, the dashboard module configured to perform the processing steps of:

collecting, from a plurality of sources in a location within the medical care setting, electronic medical to of a patient in the location within the medical care setting, the plurality of sources including a physical exam of the patient and medical devices communicatively connected to the patient dashboard system, the electronic medical data comprising a patient type determined based on an injury or illness of the patient;

storing the electronic medical data of the patient in a data repository;

selecting, based on the patient type and from a plurality of guidelines for treatment of patients, a subset of the plurality of guidelines pertinent to the injury or illness of the patient;

filtering the stored electronic medical data of the patient according to the patient type, wherein the filtering produces filtered medical data of the patient, wherein the filtered medical data is associated with the injury or illness of the patient;

determining, from the subset of the plurality of guidelines, a first set of location-specific guidelines based on the location of the patient;

analyzing the filtered medical data of the patient associated with the injury or illness of the patient according to the first set of location-specific guidelines pertinent to the injury or illness of the patient;

generating, based on the analyzing, one or more recommendations for a medical treatment of the injury or illness of the patient;

determining, based on the patient's changing from the location to a different area, a second set of location-specific guidelines;

applying the second set of location-specific guidelines to the filtered medical data of the patient, wherein the applying produces an updated recommendation; and automatically updating, in near real-time, the display device data with the updated recommendation.

9. The patient dashboard system of claim 8, wherein analyzing the filtered medical data of the patient further comprises categorizing the patient.

10. The patient dashboard system of claim 8, wherein the medical care setting comprises a hospital, a trauma center, an emergency room, a floor, an intensive care unit, or a pre-hospital setting.

11. The patient dashboard system of claim 8, wherein the medical devices comprise at least one of an imaging device, labs, medications, a heart monitor, a patient chart, a vital sign monitor, or an intravenous (IV) pump.

12. The patient dashboard system of claim 8, wherein the processing steps further comprise:
prior to applying the second set of location-specific guidelines to the filtered medical data of the patient, discontinuing the first set of location-specific guidelines.

13. The patient dashboard system of claim 8, wherein the location comprises an intensive care unit, an emergency room, an operating room, a patient room, or a monitoring room and wherein the area comprises an intermediate care program (ICP) or a neurosurgery unit.

14. A computer program product comprising a non-transitory computer-readable medium storing instructions translatable by a processor of a patient dashboard system for:
collecting, from a plurality of sources in a location within a patient care setting, electronic medical data of a patient in the location within the patient care setting, the plurality of sources including a physical exam of the patient and medical devices communicatively connected to the patient dashboard system, the electronic medical data comprising a patient type determined based on an injury or illness of the patient;

storing the electronic medical data of the patient in a data repository;

selecting, based on the patient type and from a plurality of guidelines for treatment of patients, a subset of the plurality of guidelines pertinent to the injury or illness of the patient;

filtering the stored electronic medical data of the patient according to the patient type, wherein the filtering produces filtered medical data of the patient, wherein the filtered medical data is associated with the injury or illness of the patient;

determining, from the subset of the plurality of guidelines, a first set of location-specific guidelines based on the location of the patient;

analyzing the filtered medical data of the patient associated with the injury or illness of the patient according to the first set of location-specific guidelines pertinent to the injury or illness of the patient;

generating, based on the analyzing, one or more recommendations for a medical treatment of the injury or illness of the patient;

determining, based on the patient's changing from the location to a different area, a second set of location-specific guidelines;

applying the second set of location-specific guidelines to the filtered medical data of the patient, wherein the applying produces an updated recommendation; and automatically updating, in near real-time, the display device, with the updated recommendation.

15. The computer program product of claim 14, wherein the patient dashboard system comprises a video display device, a monitor, an auto-updated device, or a presentation device.

16. The computer program product of claim 14, wherein the patient care setting comprises a hospital, a trauma center, an emergency room, a floor, an intensive care unit, or a pre-hospital setting.

17. The computer program product of claim 14, wherein the medical devices comprise at least one of an imaging device, labs, medications, a heart monitor, a patient chart, a vital sign monitor, or an intravenous (IV) pump.

18. The computer program product of claim 14, wherein analyzing the filtered medical data of the patient further comprises categorizing the patient.

19. The computer program product of claim 14, wherein the instructions are further translatable by the processor for:

prior to applying the second set of location-specific guidelines to the filtered medical data of the patient, discontinuing the first set of location-specific guidelines.

20. The computer program product of claim 14, wherein the location comprises an intensive care unit, an emergency room, an operating room, a patient room, or a monitoring room and wherein the area comprises an intermediate care program (ICP) or a neurosurgery unit.

* * * * *